(12) United States Patent
O'Rear et al.

(10) Patent No.: US 7,402,187 B2
(45) Date of Patent: Jul. 22, 2008

(54) RECOVERY OF ALCOHOLS FROM FISCHER-TROPSCH NAPHTHA AND DISTILLATE FUELS CONTAINING THE SAME

(75) Inventors: Dennis J. O'Rear, Petaluma, CA (US); Thomas Van Harris, Solano, CA (US); Cong-Yan Chen, Kensington, CA (US)

(73) Assignee: Chevron U.S.A. Inc., San Ramon, CA (US)

(*) Notice: Subject to any disclaimer, the term of this patent is extended or adjusted under 35 U.S.C. 154(b) by 286 days.

(21) Appl. No.: 10/267,406

(22) Filed: Oct. 9, 2002

(65) Prior Publication Data
US 2004/0068923 A1   Apr. 15, 2004

(51) Int. Cl.
C10L 1/18   (2006.01)
(52) U.S. Cl. ......................................................... 44/451
(58) Field of Classification Search .................... 44/451
See application file for complete search history.

(56) References Cited

U.S. PATENT DOCUMENTS

| | | | |
|---|---|---|---|
| 4,293,220 A | 10/1981 | Denton et al. | |
| 4,384,148 A | 5/1983 | Schmidt | |
| 4,962,239 A | 10/1990 | Bell et al. | |
| 5,151,371 A | 9/1992 | Quimby et al. | |
| 5,231,233 A | 7/1993 | Le et al. | |
| 5,258,560 A | 11/1993 | Marker | |
| 5,405,814 A | 4/1995 | Beech, Jr. et al. | |
| 5,689,031 A | 11/1997 | Berlowitz et al. | |
| 5,766,274 A | 6/1998 | Wittenbrink et al. | |
| 5,814,109 A | 9/1998 | Cook et al. | |
| 5,895,506 A | 4/1999 | Cook et al. | |
| 6,017,372 A | 1/2000 | Berlowitz et al. | |
| 6,056,793 A * | 5/2000 | Suppes | 44/446 |
| 6,822,131 B1 * | 11/2004 | Berlowitz et al. | 585/733 |
| 6,824,574 B2 | 11/2004 | O'Rear et al. | |
| 2002/0005009 A1 | 1/2002 | Wittenbrink et al. | |

FOREIGN PATENT DOCUMENTS

| | | |
|---|---|---|
| EP | 1 138 751 A2 | 10/2001 |
| EP | 1 270 706 | 1/2003 |
| FR | 2 650 289 | 7/1990 |
| GB | 2364712 | 6/2002 |
| WO | 96/23855 | 8/1996 |
| WO | 97/04044 | 2/1997 |
| WO | WO-01/46347 A1 | 6/2001 |
| WO | WO-01/46348 A1 | 6/2001 |
| WO | 03/044133 A2 | 5/2003 |

OTHER PUBLICATIONS

United Kingdom Search Report dated Sep. 28, 2004.
Dutch Search Report dated Dec. 8, 2004.
United Kingdom search report dated Feb. 17, 2004.

* cited by examiner

*Primary Examiner*—Cephia D Toomer
(74) *Attorney, Agent, or Firm*—Crowell & Moring LLP

(57) ABSTRACT

Olefins and alcohols present in Fischer-Tropsch products are converted to primary and secondary alkyl alcohols having at least four carbons through acid catalyzed etherification and hydrolysis reactions. The alcohols are added to a highly iso-paraffinic distillate fuel blend, improving the lubricity of the mixture, and forming a distillate fuel with improved lubricity.

10 Claims, No Drawings

RECOVERY OF ALCOHOLS FROM FISCHER-TROPSCH NAPHTHA AND DISTILLATE FUELS CONTAINING THE SAME

This invention relates generally to a distillate fuel having improved lubricity and to a method to prepare alcohols from a Fischer-Tropsch product. More specifically, this invention relates to a method to produce primary and secondary alkyl alcohols having at least four carbons by conversion of the alcohols and olefins in a Fischer-Tropsch product through acid catalyzed etherification and hydrolysis reactions. When these alcohols are added to a highly isoparaffinic distillate fuel blend, the lubricity of the mixture is improved.

BACKGROUND OF THE INVENTION

Because of the need to reduce fuel emissions, clean-burning middle distillate fuel blends such as diesel and jet fuels are required. These distillate fuel blends can come from many sources, including Fischer-Tropsch synthesis, olefin oligomerization, hydrotreating and hydrocracking processes and combinations thereof. One existing method of creating cleaner fuels involves the severe hydroisomerization of distillate streams to form highly isoparaffinic products. In severely hydroisomerized materials, the lubricity is often low due to the absence of oxygenates, aromatics and heterocyclics such as sulfur-containing compounds. However, lubricity is required for the efficient operation of fuel delivery systems, and the need exists for an environmentally benign way of increasing the lubricity of clean distillate fuel blends. Low lubricity can lead to excessive wear of metal engine parts which can result in poor engine performance, additional pollution, lower fuel mileage and early replacement of engine parts.

Fuel lubricity can be measured by one of two methods: ASTM D6078 or ASTM D6079. ASTM D6078 is a scuffing load ball-on-cylinder lubricity evaluator method (SLB-OCLE) and D6079 is a high frequency reciprocating rig method (HFRR). Fuels having a D6078 lubricity of less than about 2,000 grams are not likely to prevent excessive wear in injection equipment, while fuels with values above about 3,100 grams should provide sufficient lubricity in all cases. If D6079 is used, fuels with values above about 600 microns are not likely to prevent excessive wear while fuels with values below about 450 microns should provide sufficient lubricity in all cases.

The reproducibility limit for ASTM D6078 is ±900 grams, and the reproducibility limit for ASTM D6079 is ±80 microns. Thus, an increase in the D6078 value of about 900 grams or more or a decrease in the D6079 value of about 80 microns or more demonstrates an absolute improvement in lubricity. However, D6078 increases of about 225 grams or D6079 decreases of about 20 microns or more provide an acceptable measure of a fuel with improved lubricity provided that the measurements are made on the same equipment and a sufficient number of measurements are made.

Higher alkyl alcohols, i.e., alcohols with at least four carbons, are known to improve the lubricity and stability of distillate fuel blends. These higher alcohols are also used in detergents and plasticizers, and the selling price for such alcohols is often more than one dollar per kilogram, significantly more than the price for fuels. Thus, there is a strong economic incentive to recover the alcohols present in distillate fuel blends rather than allow them to be converted into fuels.

Some primary higher alkyl alcohols are created during the normal production of distillate fuel blends. For example, in a Fischer-Tropsch synthesis, a synthetic gas composed mostly of CO and $H_2$ is reacted in the presence of a catalyst to form a wide range of gaseous and liquid hydrocarbon products including a paraffinic wax. Alcohols and olefins are normally present in some Fischer-Tropsch products. However, the amount of alcohols normally produced during a Fischer-Tropsch synthesis is not enough to raise the lubricity of the isoparaffinic distillate fuel blends to an acceptable level.

The Fischer-Tropsch synthesis provides a light naphtha stream containing low molecular weight linear paraffins and olefins as well as oxygenated compounds such as alcohols. These naphthas are too volatile for incorporation into distillate transportation fuels and their levels of olefins and oxygenates makes them unsuitable for use in gasoline or as a petrochemical plant feed. They are considered less valuable than distillate fuels but it is not possible to vary reaction conditions to selectively eliminate production of light naphthas and increase production of distillate transportation fuels. In conventional practice, the light naphthas must be further refined to reduce the content of olefins and oxygenates in order to provide a salable naphtha.

The use of alcohols, and specifically higher primary alkyl alcohols, to improve lubricity in highly isoparaffinic distillate fuel blends has been disclosed in a variety of patents. U.S. Pat. No. 5,814,109 describes a process for producing higher alcohol-containing additives for distillate fuel blends through a Fischer-Tropsch reaction. These additives are useful for improving the cetane number, lubricity, or both, of a mid-distillate diesel fuel. U.S. Pat. No. 5,766,274 describes the production of a clean jet fuel distillate by hydroisomerizing only the heavier portion of a Fischer-Tropsch wax and blending with the lighter portion which retains most of the alcohols in the Fischer-Tropsch wax product. Because most of the alcohols are retained, the blended distillate has a higher lubricity than if the entire wax were hydrotreated. U.S. Pat. No. 5,689,031 describes the production of a clean distillate, for use as a diesel fuel, by hydroisomerizing a portion of a Fischer-Tropsch wax. Again, because only a portion of the wax is hydrotreated, some of the alcohols are preserved in the untreated portion thereby increasing the lubricity of the distillate. WO 01/46347 A1 discloses significantly improved reduced particulate emission performance of exhausts of vehicles powered by fuel combustion both at high and low loads by adding oxygenates or other hydrocarbon components in a diesel fuel composition comprising a major amount of a base fuel and a relatively minor amount of at least one chemical component other than that generated in a refinery process stream. WO 01/46348 discloses a fuel composition comprising a base fuel having 50 ppm or less or sulfur, 10% or less of olefin, 10% or less of ester and at least 1 wt. % of oxygenate chosen from certain alcohols(s) and ketone(s) and having no other oxygen atom in its structure, with improved reduction of particulate emission without using further additives such as cyclohexane or peroxides or aromatic alcohol and with little to no increase in nitrogen oxide (NOx) emission at high engine loads.

However, in each of these processes, olefins are retained in addition to the alcohols. Frequently, the olefins outnumber the alcohols on a molar basis. The presence of olefins is undesirable and can lead to thermal stability problems, and also to the formation of gums. A need exists for a distillate diesel or jet fuel blend with improved lubricity through the use of alcohols, but without the inclusion of olefins in the final product. A low level of olefins is defined as a molar ratio of total olefin to total alcohol below 0.5, preferably below 0.25 and most preferably below 0.1. Ideally, the olefin content should be below the limit of detection.

In addition, a need exists for methods of recovering alcohols from a distillate fuel product and methods of removing unwanted olefins without the use of hydrogen, which is expensive.

Techniques are well known in the art for converting olefins to ethers, and then to alcohols. For example, formation of di-isopropyl ether from alcohols and olefins is well known. U.S. Pat. No. 5,405,814 describes the conversion of light olefins, especially propylene, to a mixture of alcohols and ethers. U.S. Pat. No. 4,962,239 discloses the synthesis of ethers from alcohols and olefins using Zeolite MCM-22. U.S. Pat. No. 5,231,233 discloses the synthesis of ethers and/or alcohols using Zeolite MCM-36. U.S. Pat. No. 5,285,560 discloses a catalytic distillation reactor instead of a fixed bed reactor for synthesizing ethers. The disclosures of these patents are incorporated herein by reference. However, these processes focus on the production of lower alkyl ethers that are more volatile than their starting alcohols or olefins, so the ethers could not be easily separated from the mixture by distillation. Also, these processes do not address lubricity concerns or olefin content.

Often, the ethers and alcohols formed by known processes are of relatively low molecular weight, and sometimes environmentally harmful. For example, the dangers of methyl tertiary butyl ether (MTBE) and methyl tertiary amyl ether (TAME) when used as blend components in gasoline are well known. MTBE and TAME contaminate underground aquifers when gasoline spills or leaks. MTBE and TAME have significant water solubility, and eventually hydrolyze to form tertiary butyl alcohol and tertiary amyl alcohol. Because these alcohols and their parent ethers lack protons on the carbon in the non-methyl group adjacent to the oxygen in the ether, they are not very biodegradable. Thus, they partition into the underground water phase and remain there for a long time. The lack of reactive protons in this position of MTBE and TAME is consistent with their chemical structural identity of being "tertiary" alcohols.

It is therefore an object of the present invention to improve the lubricity of middle distillate fuels such as diesel and jet fuels by the use of higher primary and secondary alkyl alcohols while minimizing the presence of olefins, and to develop a process for making such a distillate fuel with good lubricity.

It is another object of the present invention to increase the lubricity of middle distillate fuel blends in an environmentally benign way. A further object of the invention is to produce a mixture of primary and secondary alcohols as a pure product substantially free of hydrocarbons. Yet another object of the invention is to convert the olefins in Fischer-Tropsch naphtha and distillate products without the use of hydrogen.

These and other objects of the present invention will become apparent to the skilled artisan upon a review of the following description and the claims appended thereto.

SUMMARY OF THE INVENTION

The objectives of the invention are attained by distilling a Fischer-Tropsch product to obtain a fraction containing olefins and alcohols, subjecting the fraction to acid-catalyzed etherification, distilling the etherified product to separate the ethers, hydrolyzing the ethers to produce alcohols and optionally purifying the alcohol mixture and recovering alcohols. A diesel or jet fuel or blend stock with good lubricity can be made from a highly paraffinic distillate fuel blend component having at least 50 wt. %, preferably 70 wt. %, isoparaffins with a lubricity as measured by ASTM D6078 of less than about 3100 grams, or 600 microns or less as measured by ASTM D6079, by adding a sufficient amount of at least one primary or secondary alkyl alcohol of the formula R—OH where R is an alkyl group of at least 4 carbon atoms, such that the resultant blend has its lubricity improved by at least about 225 grams, preferably by at least about 450 grams (ASTM D6078), and where the molar ratio of olefins to alcohols in the diesel or jet fuel or blend stock is about 0.5 or less, and preferably 0.1 or less.

In a preferred embodiment, a syngas obtained from a source such as natural gas, a petroleum fraction, coal or shale is reacted in a Fischer-Tropsch synthesis to obtain a light naphtha fraction containing paraffins, alcohols and olefins and a heavier carbonaceous fraction. The naphtha fraction is treated to convert the olefins and alcohols into higher dialkyl ethers while the heavier fraction is hydrotreated to form a middle distillate fuel product containing a high proportion of isoparaffins. The ethers are recovered, converted into alcohols and added to the middle distillate fuel product to provide increased yields of a mid-distillate fuel blend having suitable lubricity and a very low olefin content. This invention meets the goals of creating a clean diesel or jet distillate fuel blend with good lubricity, and wherein the alcohols and ethers created are environmentally benign.

DETAILED DESCRIPTION OF THE INVENTION

Environmentally benign alcohols, useful for improving the lubricity of distillate fuel blends, can be recovered from Fischer-Tropsch fractions which contain mixtures of $C_{4+}$ olefins and alcohols. These mixtures can be reacted to produce ethers which are higher boiling than the feedstock olefins and alcohols. The ethers can be recovered by distillation and the recovered ethers converted back to alcohols by the reverse of the etherification process, i.e., hydrolysis.

Boiling points of key alkyl alcohols and dialkyl ethers are shown in the following table.

| Carbon No. | Species | Alcohol | Boiling Point, °C. | Ether | Boiling Point, °C. |
|---|---|---|---|---|---|
| 1 | Methyl | Methanol | 39 | Di-methylether | −25 |
| 2 | Ethyl | Ethanol | 78 | Di-ethylether | 35 |
| 3 | Propyl | n-Propanol | 97 | Di-n-propylether | 91 |
|  |  | i-Propanol | 87 | Di-i-propylether | 69 |
| 4 | Butyl | 1-Butanol | 117 | Di-n-butylether | 142 |
|  |  | 2-Butanol | 99 | Di-2-butylether | 120 |
| 5 | Pentyl | 1-Pentanol | 137 | Di-1-pentylether | 190 |
|  |  | 2-Pentanol | 118 | Di-2-pentylether | 172 |
| 6 | Hexyl | 1-Hexanol | 158 | Di-1-hexylether | 223 |
| 7 | Heptyl | 1-Heptanol | 177 | Di-1-heptylether | 258 |
| 8 | Octyl | 1-Octanol | 194 | Di-1-octylether | 286 |

As shown, alcohols containing four or more carbons form ethers which are higher boiling than the corresponding alcohol. The same is true for the relationship between the boiling point of the ether and the olefin. This permits a process in which higher dialkyl ethers can be formed from a Fischer-Tropsch product containing a mixture of olefins, alcohols, and unreactive paraffins. The product ethers can then be separated from the unreactive paraffins in the Fischer-Tropsch product by simple distillation. The boiling range of the Fischer-Tropsch product should be narrow enough so that at least a portion of the product ethers can be separated from the unreactive paraffins by distillation. Furthermore, the boiling range of the Fischer-Tropsch product should be narrow enough that when the olefins and alcohols contained in it are converted to ethers, at least a portion of the product ethers will have a boiling point higher than the end boiling point of the Fischer-Tropsch product.

Light olefins are converted into ethers using an acid catalyst and water. The first step is hydration of the olefin to form an alkyl alcohol. As shown by the following, this reaction consumes water:

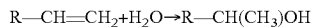
$$R-CH=CH_2 + H_2O \rightarrow R-CH(CH_3)OH$$

where R is a higher alkyl group.

The next step is the hydration of the alcohol to form a dialkyl ether and generate water:

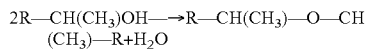
$$2R-CH(CH_3)OH \rightarrow R-CH(CH_3)-O-CH(CH_3)-R + H_2O$$

Olefins and alcohols can also react directly to form an ether. This reaction neither uses nor produces water, and is often referred to as a condensation:

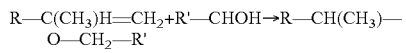
$$R-C(CH_3)H=CH_2 + R'-CHOH \rightarrow R-CH(CH_3)-O-CH_2-R'$$

As shown above in reaction (1), the hydrated olefin is not a primary alcohol, but an internal or secondary alcohol. The ethers derived from olefins also will not be linear, as shown above in reactions (2) and (3). Alcohols present in Fischer-Tropsch naphtha are mostly primary alcohols. While it depends somewhat on the conditions and catalysts used in the dehydration step, the ethers derived from primary alcohols will likely be linear. So when a mixture of olefins and primary alcohols are present in a Fischer-Tropsch naphtha, the ethers obtained therefrom will be a mixture of linear and branched structures. Upon recovery and hydrolysis, they will form a mixture of primary and secondary alcohols. Because dialkyl ethers with four or more carbons will have higher boiling points than the corresponding alkyl alcohols, the ethers can be separated from the remaining unreactive paraffins by distillation. The ethers can then be hydrolyzed into alcohols with the use of an acid catalyst and the alcohols further purified through distillation, drying, extraction or adsorption.

Water may or may not be needed to convert an initial mixture to ethers. Fischer-Tropsch naphtha contains a mixture of both olefins and alcohols. Thus, the need for water and the amount of water to be added depends on the analysis of the naphtha. If there is an excess of olefins relative to alcohols, water must be added. If there is an excess of alcohols relative to olefins, water addition will not be needed since water will be formed during the reaction.

The stoichiometric conversion of a pure olefin into an ether generally requires about 0.5 moles of water per mole of olefin. However, to minimize an olefin oligomerization reaction, the desired effective ratio of water to olefin ranges from about 0.1 to about 3, preferably about 0.25 to about 1.0, and most preferably about 0.5 to about 0.6.

If alcohols and ethers are present in the feedstock, various equilibrium relationships must also be considered. A mole of alcohol can dehydrate to form a mole of water and a mole of olefin. A mole of ether can dehydrate to form a mole of water and two moles of olefin. Thus, the effective amount of water in the reactor can be calculated as moles of water added to the feedstock plus moles of alcohol in the feedstock plus moles of ether in the feedstock and the effective amount of olefins in the reactor can be calculated as moles of olefin in the feedstock plus moles of alcohol in the feedstock plus two times the moles of ether in the feedstock. All quantities are moles of species per mole of feedstock. These definitions of the effective amounts of water and olefins in the reactor can be used with the preferred ranges of the effective ratio of water to olefin to determine how much, if any, water must be added to the feedstock. In equation form, Effective ratio of water to olefin=(Water+Ether+Alcohol)/(Olefin+Alcohol+2×Ether)

where all quantities are moles of species per mole of feedstock, "Ether," "Alcohol" and "Olefin" refer to moles in the feedstock, and "Water" refers to moles added to the feedstock.

The content of alcohols in the distillate fuels can be determined by several techniques that are well known in the field. For example, Infrared (IR) or Gas Chromatography Infrared (GC/IR) can be used. Petrospec GS-1000 is a commercial IR analyzer that is designed for analysis of ethers in gasoline and is suitable, with minor modifications, for the measurement of alcohols in distillate fuels. U.S. Pat. No. 5,895,506 describes the use of IR techniques to monitor various oxygenate and olefin classes in Fischer-Tropsch products. Gas Chromatography-Atomic Emission Detection (GC-AED) could also be used. GC-AED is a Gas Chromatography (GC) separation system coupled with an oxygen elemental detector. GC-AED is described in U.S. Pat. No. 4,293,220, with further refinements in U.S. Pat. No. 5,151,371. The concentration of the ethers can also be determined by supercritical fluid chromatography (SFC). ASTM D4185 can be adapted for this analysis. For all these methods, suitable calibration should be done using pure alcohols and a distillate fuel that is of approximately the same composition as the non-ether components. The preferred methods are IR, GC-IR or GC-AED. The most preferred method is GC-IR.

The content of olefins in the distillate fuel can also be determined by several well-known techniques. For example, IR, GC-IR, or GC-AED can be used. Olefins can be monitored by GC-AED because their carbon-to-hydrogen (C/H) ratios are greater than those of similar carbon number saturates. However, cyclo-paraffins interfere with this approach since they have identical C/H ratios. Supercritical fluid chromatography (SFC) as practiced in ASTM D5605 for olefins in gasoline, can be modified for olefin content in other distillate cuts. The olefins are selectively retained by a silver-loaded column. The concentration of the ethers can also be determined by SFC through comparison with pure standards due to their longer retention times. ASTM D4185 can be adapted for this analysis. For all these methods, suitable calibration should be done using pure alcohol and olefins standards and a distillate fuel that is of approximately the same composition as the non-ether components. The preferred methods are IR, GC-IR or CG-AED. The most preferred method is GC-IR.

An acid catalyst is required for both ether formation and ether hydrolysis. The acid catalyst should be regenerable and not affected by the presence of water. The preferred acid catalysts fall into two types: solid acid catalysts (zeolites, acidic clays, silica aluminas, etc.) and resin catalysts. Acid catalysts such as aluminum chloride, sulfuric acid, phosphoric acid, hydrofluoric acid, and other bulk acids are not preferred because they either react with water, or are diluted by it.

Zeolites are very rugged and can be regenerated by use of oxidation. The preferred zeolites contain at least some pores that have 10-ring or larger pores. Preferred zeolites for alcohol condensation to ethers contain 12-ring or larger pores. Preferred zeolites for olefin hydration to alcohols contain 10-ring or larger pores. Examples of zeolites that have 12-ring or larger pores include Beta, Y, L, Mordenite, MCM-22, MCM-36, ZSM-12, SSZ-25, SSZ-26, and SSZ-31. Examples of zeolite that have 10-ring or larger pores include ZSM-5, ZMS-11, ZSM-22, ZSM-23, ZSM-35, Ferrierite, SSZ-20, SSZ-32, and Theta-1. Examples of zeolites that contain both 10-ring and 12-ring pores include SSZ-25, SSZ-26, and MCM-22. The use and selection of zeolites permits the olefin hydration to proceed rapidly, and secondary ethers to form. However, the concentration of acidic sites in zeolites is moderate, and they require the use of temperatures above 125 to 600° F. In contrast, resin catalysts have a large number of acidic sites and can be operated at comparatively lower temperatures (150 to 350° F.). However, resin catalysts are not as rugged as zeolites, and cannot be regenerated by oxidation. Either type of acid catalyst may be used to form ethers, but the solid acid catalysts, especially zeolites, are preferred for alcohol-rich feeds. Resins are preferred for olefin-rich feeds.

The broad and preferred conditions for use with solid acid catalysts are shown in the following table.

|  | Alcohol dehydration to ethers and combined hydration of olefins to ethers | | Ether hydrolysis to form alcohols | |
| --- | --- | --- | --- | --- |
|  | Broad | Preferred | Broad | Preferred |
| Temperature, ° F | 125-600 | 300-400 | 125-600 | 300-400 |
| Pressure, psig | >250 | 250-1500 | >250 | 250-1500 |
| LHSV, hr$^{-1}$ | >0.1 | 0.2-2.0 | >0.1 | 0.5-2.0 |
| Eff. Water/Olefin | 0.1-3 | 0.25-1 | >5 | >10 |

Preferably, the pressure should be sufficient to maintain all the reactants in the liquid phase under reaction conditions. The LHSV is expressed on the basis of the sum of the rates of the reactive olefin, alcohols and water, and does not include paraffins. For alcohol dehydration to ethers and combined hydration of olefins and alcohol mixtures to ethers, the most preferred effective ratio of water to olefin is about 0.5 to 0.6. This range can be used to determine how much, if any, additional water must be added to the feedstock.

The broad and preferred conditions for resin catalysts are shown in the next table.

|  | Alcohol dehydration to ethers and combined hydration of olefins to ethers | | Ether hydrolysis to form alcohols | |
| --- | --- | --- | --- | --- |
|  | Broad | Preferred | Broad | Preferred |
| Temperature, ° F | 150-350 | 200-275 | 150-350 | 200-275 |
| Pressure, psig | >250 | 250-1500 | >250 | 250-1500 |
| LHSV, hr$^{-1}$ | >0.1 | 0.2-2.0 | >0.1 | 0.5-2.0 |
| Eff. Water/Olefin | 0.1-3 | 0.25-1 | >5 | >10 |

For alcohol dehydration to ethers and combined hydration of olefins and alcohol mixtures to ethers, the most preferred effective ratio of water to olefin is about 0.5 to 0.6.

The alcohols recovered from the hydrolysis process will be a mixture of primary and secondary alcohols. Minor amounts of other branched alcohols may also be present. For some products, it may be desirable to separate the primary alcohols, the most valuable alcohols, from the other species. The separation of linear hydrocarbonaceous compounds (including the desired primary alcohols) from non-linear hydrocarbonaceous compounds is well known in the industry. Zeolites can be used to selectively adsorb the linear hydrocarbonaceous compounds from the mixture. The preferred zeolites will have 8-ring pores which will permit the adsorption of linear hydrocarbonaceous compounds but not the non-linear compounds. An A type zeolite is most commonly used, and the most preferred form of an A type zeolite is one that has been ion exchanged to narrow the pores and improve separation.

Various processes have been proposed for separation of n-paraffins and isoparaffins using molecular sieves. These processes can be used with or without minor adaptation for the separation of primary alcohols from branched alcohols. Typical examples are the Molex process (U.O.P.), Iso-Siv process (U.C.C.) and TSF process (TEXACO Dev.). Basically, according to these processes, a mixed hydrocarbon feed material is contacted with molecular sieves of 5 Angstroms in gaseous or liquid phase to adsorb straight-chain hydrocarbons and then the straight-chain compounds are desorbed at a low pressure or a high temperature, usually with the aid of purge gas or desolvents such as n-pentane or isooctane. In this case, adsorbing and desorbing conditions usually involve temperatures in the range from room temperature to 350° C., preferably 100 to 320° C., and pressures from 1 to 60 kg/cm$^2$ or higher.

The etherification/hydrolysis of the present invention converts the unwanted olefins in a Fischer-Tropsch product into alcohols without the use of hydrogen, which can be expensive when provided in remote locations. Accordingly, the source of the olefins and alcohols can be any Fischer-Tropsch product, not just Fischer-Tropsch naphtha. The key requirement is that the boiling range of the feedstock be narrow enough that when the olefins and alcohols contained in it are converted to ethers, at least a portion of the product ethers will have a boiling point higher than the end boiling point of the feed. Thus one can start with a distillate fraction that contains olefins and alcohols, convert them to ethers, separate the ethers by distillation, convert the ethers back to alcohols (which will not contain olefins), and then blend the alcohols back into the fuel. This also increases the amount of alcohols to be blended into the fuel because the olefins are also converted into ethers. The alcohols derived from this route will be a mixture of primary and secondary alcohols.

Instead of using the above described method to recover primary alcohols, an alternative approach would be to selectively saturate the olefins in the Fischer-Tropsch fraction by hydrogenation without converting the primary alcohols. The primary alcohols would then be etherified as described above, the ethers recovered by distillation, and then hydrolyzed to re-form primary alcohols. Technology is well known in the art for selective hydrogenation of olefins to form inert paraffins.

This invention describes the production of higher alkyl alcohols, which can be used to improve the lubricity of middle distillate paraffinic fuel blends, from Fischer-Tropsch products, preferably Fischer-Tropsch naphtha. These alcohols can be added to highly-paraffinic distillate fuel blends containing at least 50 wt. %, preferably 70 wt. %, isoparaffins having low lubricity to raise the lubricity as measured by ASTM D6078 by at least about 225 grams, preferably 450 grams. The middle distillate fuel blend can come from a Fischer-Tropsch synthesis, olefin oligomerization, hydrotreating or hydrocracking processes or combinations thereof. The final blend should contain at least about 10 parts per million (ppm) oxygen as alcohol, preferably between about 100 ppm and about 1 wt. % oxygen as alcohol, and more preferably between about 1000 ppm and about 0.5 wt. % oxygen as alcohol.

Because the alkyl alcohols are primary or secondary, and not tertiary, they are environmentally benign. Due to their higher molecular weights, the alcohols are not as water soluble as lower molecular weight alkyl alcohols, and since there is a proton on the non-methyl carbon adjacent to the oxygen, the alkyl alcohols are more reactive and thus, more biodegradable. In addition, distillate diesel fuel blends mixed with these alcohols will have higher cetane numbers, and better seal swell properties and jet fuel blends will have higher smoke points. Finally, removing many of the alcohols from the Fischer-Tropsch product reduces the amount of refining necessary before the product can be sold.

In an alternative embodiment of the present invention, instead of blending at least a portion of the produced alcohols into the Fischer-Tropsch product from which they were derived, at least a portion of the produced alcohols may be sold without further processing. There may be more value in selling the alcohols independently rather than using them as a fuel additive. These alcohols will be a mixture of primary and secondary alcohols. If pure primary alcohols are desired, they can be separated by adsorption over a molecular sieve.

The invention will now be illustrated by the following examples which are intended to be merely exemplary and in no manner limiting.

EXAMPLE 1

Identification of Catalysts for Ether Synthesis From Alcohols

The following batch experiment was used to identify preferred catalysts for conversion of alcohols into ethers. For each trial, 1.0 g of catalyst was charged to a 25 mL stainless steel pressure batch reactor equipped with a magnetic stirring bar. The reactor was evacuated and backfilled with nitrogen several times. The initial pressure in the reactor was set at 560 psig by adding nitrogen gas. While under nitrogen, 5 mL of 1-butanol was added. The reactor was then heated with stirring for 18 hours at 200° C. Upon heating, the pressure rose to approximately 200-250 psig. At the end of the heating period, the reactor was cooled to room temperature and then to dry ice temperature. Through a rubber septum 5 mL of n-hexane was added. Next, ~2 g of n-heptane was accurately weighed in to serve as an internal standard. The product was then removed from the reactor and analyzed by gas chromatography.

Samples of various acidic catalysts were evaluated in this batch test with the following results.

| Trial No. | Catalyst Identification | Zeolite Ring Aperture size | Alpha Value | 1-Butanol conversion, % | Butene selectivity, % | Di-n-butyl ether selectivity, % |
| --- | --- | --- | --- | --- | --- | --- |
| 1 | CBV-760 Y zeolite | 12 | 28 | 77.9 | 5.6 | 94.4 |
| 2 | CBV-9010 Y zeolite | 12 | 3 | 83.3 | 9.5 | 90.5 |
| 3 | Al$_2$O$_3$-bound SSZ-32 | 10 | ~300 | 44.6 | 55.2 | 44.8 |
| 4 | Al$_2$O$_3$-bound ZSM-5 | 10 | 300 | 91.8 | 43.6 | 56.4 |

The preferred catalysts for this application will have the highest possible values for 1-butanol conversion and selectivity for formation of di-n-butyl ether. The catalysts will have conversions and selectivities equal to or greater than 50%, preferably equal to or greater than 75%, and most preferably equal to or greater than 90%, under conditions of this test.

EXPERIMENT 2

Olefin Hydration

The flow-type microunits used in this study were equipped with a stainless steel fixed bed reactor and an on-line GC. The catalysts studied for 1-butene hydration are as follows: Alumina base from Condea Chemie, calcined in air at 950° F. for 4 hours, Zeolite Y (CBV 901, no binder), Zeolite Al-SSZ-33, Zeolite Al-SSZ-42, Amberlyst Resin XN-1010, and Amberlyst Resin 15

The zeolite catalysts (0.24-0.26 g=4.0 cc each) were crushed to 24-60 mesh and, prior to the reaction, dehydrated in a N$_2$ flow (200 cc/min) at 662° F. (350° C.) overnight.

The products were analyzed with an on-line GC using a HP-1 capillary column and a Flame Ionization Detector (FID). The FID Response Factors (RF) for 1-butanol, di-n-butyl ether and hydrocarbons were determined by assuming hydrocarbon RF=1.

| Component | Response Factor (RF) |
| --- | --- |
| 1-butanol | 1.4663 |
| di-n-butyl ether | 1.2626 |
| octane(as internal standard) | 1.0000 |

The response factors are defined so that:

$$W_1 = Wfoctane \times (A_1/A_{octane}) \times (RF_i/RF_{octane})$$

where $W_1$ stands for the weight of component i, $A_i$ for the GC area of component i and $RF_i$ for the Response Factor of component i with $RF_{octane}=1$ for the internal standard octane.

Results of 1-Butene Hydration

| Experiment | 1 | 2 | 3 | 4 |
| --- | --- | --- | --- | --- |
| Catalyst | Al$_2$O$_3$ | Y Zeolite | SSZ-33 | SSZ-33 |
| Temp., ° F | 482-572 | 392 | 392 | 347 |
| Pressure, psig | 1500 | 250 | 1500 | 1500 |
| H$_2$O/1-butene | 2 | 2 | 1.1 | 1.1 |
| LHSV, hr$^{-1}$ | 0.41-0.5 | 0.5 | 0.41 | 0.41 |
| 1-butene = Conv % | No Rxn | 3 | ~16 | 9.5 |
| Selectivities | | | | |
| Butanol | — | 100 | 62 | 84 |
| Ether | — | 0 | 38 | 16 |
| Oligomer | — | 0 | 0 | 0 |

| Experiment | 5 | 6 | 7 | 8 |
| --- | --- | --- | --- | --- |
| Catalyst | SSZ-42 | SSZ-42 | SSZ-42 | Amber. 15 |
| Temp., ° F | 302 | 392 | 392 | 212 |
| Pressure, psig | 1500 | 1500 | 1500 | 1500 |
| H$_2$O/1-butene = | 1.1 | 1.1 | 12 | 12 |
| LHSV, hr$^{-1}$ | 0.41 | 0.41 | 0.41 | 0.5 |
| 1-butene = Conv. % | 8 | 16 | 16 | ~50 |
| Selectivities | | | | |
| Butanol | 75 | 62 | 62 | 100 |
| Ether | 25 | 38 | 38 | 0 |
| Oligomer | 0 | Trace | 0 | 0 |

From these results, it can be concluded that the preferred catalysts for olefin hydration to form alcohols is a non-zeolitic catalyst such as a resin. By selection of the appropriate conditions, conversions of light olefins in excess of 50% can be obtained with selectivities to alcohols in excess of 80%, preferably in excess of 90%. Conditions which maximize the selectivity to alcohols include an effective ratio of water to olefin in excess of 2 preferably in excess of 5 and most preferably in excess of 10. Pressures should be as high as possible, preferably in excess of 250 psig, and most preferably in excess of 1250 psig.

If ethers are the desired product from a single-step reaction either a resin catalyst or a zeolite can be used. The preferred zeolites have as high of an acid strength as possible and contain 12-ring pores. High acid strength is obtained by having a $SiO_2/Al_2O_3$ molar ratio in excess of 4 preferably in excess of 10, more preferably in excess of 20, and even more preferably in excess of 40. The effective ratio of water to olefin should be between 0.1 and 3.

EXPERIMENT 3

Ether Hydrolysis

The following simple batch experiment can be used to identify catalysts useful for conversion of ethers into alcohols or olefins. Di-n-hexylether from Aldrich was used as a feedstock. Tests were performed at 200° C. using equipment and procedures described above.

Samples of various acidic catalysts were evaluated at 200° C. in this batch test with the following results. Catalysts were pelletized, crushed, and sized to 20/40 mesh. They were then calcined at 1100° F. in air. Catalyst samples (1 g) were charged to 25 mL metal batch reactors. The reactors were purged for 15 minutes with nitrogen gas at ambient pressure. Hexyl ether (5 g) and DI water (1 g) were added and the reactors sealed. The reactors were heated with stirring at 400 F for 24 hours. After cooling to ambient temperature, the reactors and contents were cooled to dry ice temperature and opened. Heptane was added as a solvent and n-octane added as an internal standard for GC analysis. Products were analyzed by GC using response factors determined for hexyl ether and hexanol.

| Catalyst Description | Alpha | Conversion, mole %, based on hexylether | Selectivity to Hexenes, % | Selectivity to Hexanol, % |
|---|---|---|---|---|
| ICR408, $Al_2O_3$-bound ZSM-5 | 300 | 5.1 | 84.3 | 15.7 |
| ICR 408 base, $Al_2O_3$-bound SSZ-32 | 300 | 8.9 | 92.7 | 7.3 |
| CBV 760 Y zeolite powder | 25 | 0.6 | 0 | 100 |
| CBV 901 Y zeolite | 3.4 | 2.9 | 0 | 100 |
| Beta zeolite powder | — | 13.8 | 88.1 | 11.9 |
| $SiO_2/Al_2O_3$ Siral 40 | 2 | 0 | — | — |
| Al-MCM-41 | | 0.1 | 17.3 | 82.7 |
| H-Al-SSZ-53 | | 5 | 31.7 | 68.3 |
| CBV-600 Y Zeolite | | 1 | 23.1 | 76.9 |
| de-Al Mordenite | | 4 | 39.5 | 60.5 |
| $NH_4$-exch SSZ-25 | | 4.3 | 42.1 | 57.9 |

If hexanol is the desired product, the preferred catalysts for this application will have the highest possible values for di-n-hexyl ether conversion and selectivity for formation of 1-hexanol. The catalysts will have selectivities to hexanol in this test equal to or greater than 50%, preferably equal to or greater than 75%, and most preferably equal to or greater than 90%. If hexene is the desired product, preferred catalysts will have the highest possible values for di-n-hexyl ether conversion and selectivity for formation of 1-hexanol. The catalysts will have selectivities to hexene in this test equal to or greater than 50%, preferably equal to or greater than 75%, and most preferably equal to or greater than 90%.

EXPERIMENT 4

Ether Hydrolysis

Experiment 4 was performed using the same equipment and procedures as described in Experiment 2 above. The catalysts studied for di-n-butyl ether hydration are as follows: Amberlyst Resin 15, Zeolite Y (CBV 901, no binder), Zeolite Al-ZSM-5 (alumina bound), Zeolite Al-SSZ-32 (alumina bound), Zeolite Al-Beta, Zeolite Al-SSZ-33, and Zeolite Al-SSZ-42.

Di-n-butyl Ether Hydration

| Experiment | 9 | 10 | 11 | 12 | 13 |
|---|---|---|---|---|---|
| Catalyst | Amb 15 | Y Zeo | Y Zeo | ZSM-5 | ZSM-5 |
| Temp., ° F. | 212 | 392 | 572 | 392 | 482 |
| Pressure, psig | 1500 | 1500 | 1500 | 1500 | 1500 |
| $H_2O$/DnB ether | 24 | 2 | 2 | 2 | 2 |
| LHSV, $hi^{-1}$ | 0.5 | 0.5 | 0.5 | 0.5 | 0.5 |
| DnB ether Conv. % | 30 | 6 | 10 | 14 | 44 |
| Selectivities | | | | | |
| Butanol | 97 | 83 | 80 | 71 | 39 |
| Butenes | 3 | 17 | 20 | 29 | 59 |
| Oligomer | 0 | 0 | 0 | 0 | 2 |
| 1-$C_4OH$ % of total Butanol | 72 | 77 | 89 | 94 | 77 |

| Experiment | 14 | 15 | 16 | 17 | 18 | 19 |
|---|---|---|---|---|---|---|
| Catalyst | SSZ-32 | SSZ-32 | Beta | Beta | SSZ-33 | SSZ-33 |
| Temp., ° F. | 392 | 482 | 392 | 482 | 392 | 482 |
| Pressure, psig | 1500 | 1500 | 1500 | 1500 | 1500 | 1500 |
| $H_2O$/DnB ether | 2 | 2 | 2 | 2 | 2 | 2 |
| LHSV, $hr^{-1}$ | 0.5 | 0.5 | 0.5 | 0.5 | 0.5 | 0.5 |
| DnB ether Conv. % | 13 | 30 | 12 | 55 | 13 | 28 |

-continued

|  | 14 | 15 | 16 | 17 | 18 | 19 |
|---|---|---|---|---|---|---|
| Selectivities |  |  |  |  |  |  |
| Butanol | 54 | 77 | 92 | 60 | 69 | 50 |
| Butenes | 46 | 23 | 8 | 33 | 31 | 36 |
| Oligomer | 0 | 0 | 0 | 7 | 0 | 14 |
| 1-C$_4$OH % of total Butanol | 83 | 68 | 98 | 88 | 89 | 89 |

From these results it can be seen that the most preferable catalyst for hydrolysis of ethers to alcohols is a non-zeolitic catalyst such as a resin. By selection of the appropriate conditions, conversions of ethers in excess of 25% can be obtained with selectivities to alcohols in excess of 80%, preferably in excess of 90%. Conditions which maximize the selectivity to alcohols include a ratio of water to ether in excess of 5 preferably in excess of 10 and most preferably in excess of 20. Pressures should be as high as possible, preferably in excess of 250 psig, and most preferably in excess of 1250 psig.

From these results it can be seen that the most preferable catalyst for conversion of ethers to olefins while minimizing formation of oligomers is a zeolitic catalyst, preferably a zeolite catalyst containing 10-ring pores, and most preferably a zeolite catalyst with non-intersecting 10-ring pores aligned in one dimension (such as SSZ-32). By selection of the appropriate conditions, conversions of ethers in excess of 25% can be obtained. Conditions which maximize the selectivity to olefins include a ratio of water to ether of less than 5 preferably less than 3 and most preferably less than 2. Pressures should be in the range of 250 to 1500 psig.

As indicated above, the highly paraffinic middle distillate diesel or jet fuel component blended with the higher alkyl alcohols may come from any available source such as oligomerization of light olefin feedstocks, hydrocracking processes, hydrotreating processes, Fischer-Tropsch syntheses and combinations thereof. Fischer-Tropsch naphtha containing olefins and alcohols is preferred. Highly paraffinic distillates are those which contain at least 50% by wt. isoparaffins, preferably 70% by wt., more preferably 80% by wt., and most preferably, 90% by wt. In general, the higher the isoparaffinic content, the more likely the distillate will have a lubricity below about 2000 grams.

Diesel and jet fuel distillates having poor lubricity may also be characterized by other characteristics such as content of aromatics, sulfur and oxygenates. Thus, a fuel with an amount of aromatic hydrocarbons including polynuclear aromatics of less than about 10% by wt., a sulfur content of less than about 10 ppm and an oxygenate content of less than about 10 ppm based on oxygen, is likely to have a lubricity below about 2000 grams.

The diesel and jet fuel distillate blends of the invention may also contain additives conventionally employed in the art. These include antioxidants, detergents, dispersants, stabilizers and the like. Suitable antioxidants include the well-known and commercially available phenolics such as 4,4'-methylene-bis(2,6-di-tertbutyl phenol) and aryl amines such as phenyl-naphthyl amine. Peroxide formation can be inhibited by adding a sulfur-containing petroleum derived feedstock in an amount sufficient to provide a sulfur content of about 1 to about 100 ppm. Peroxide content can be measured using procedures following ASTM D3703 with the exception that the Freon solvent can be replaced by isooctane. Tests confirmed that this substitution of solvents has no significant affect on the results.

While the invention has been described with preferred embodiments, it is to be understood that variations and modifications may be resorted to as will be apparent to those skilled in the art. Such variations and modifications are to be considered within the purview and the scope of the claims appended hereto.

What is claimed is:

1. A process for making a distillate fuel blend composition comprising:
   (a) obtaining a highly paraffinic distillate fuel blend component containing at least 50 wt. % isoparaffins and having a lubricity as measured by ASTM D6078 of less than about 3100 grams;
   (b) obtaining at least one primary or secondary alkyl alcohol having at least four carbon atoms by a process selected from the group consisting of alcohol condensation, condensation of alcohols with olefins, hydration of olefins, hydrolysis of ethers, distillation, and combinations thereof; and
   (c) adding a sufficient amount of at least one component containing the at least one primary or secondary alkyl alcohol having at least four carbon atoms such that the distillate fuel blend composition has a lubricity as measured by ASTM D6078 at least about 225 grams higher than that of the highly paraffinic distillate fuel blend component and such that the distillate fuel blend composition has a molar ratio of olefins to alcohols of less than about 0.5.

2. The process according to claim 1, wherein at least a portion of the at least one primary or secondary alkyl alcohol is derived from a Fischer-Tropsch process.

3. The process according to claim 1, wherein the highly paraffinic distillate fuel blend component is derived from a process selected from the group consisting of Fischer-Tropsch synthesis, olefin oligomerization, hydrotreating, hydrocracking, and combinations thereof.

4. The process according to claim 1, wherein the distillate fuel blend composition has a lubricity as measured by ASTM D6078 at least about 450 grams higher than that of the highly paraffinic distillate fuel blend component.

5. The process according to claim 1, wherein the highly paraffinic distillate fuel blend component has a lubricity as measured by ASTM D6079 of about 600 microns or less.

6. The process according to claim 1, wherein the component containing the at least one primary or secondary alkyl alcohol is derived from a Fischer-Tropsch naphtha.

7. The process according to claim 6, wherein the primary and secondary alcohols derived from a Fischer-Tropsch naphtha are less soluble in water than is methyl tertiary butyl ether.

8. The process according to claim 1, wherein the component containing the at least one primary or secondary alkyl alcohol is added such that the distillate fuel blend composition contains at least about 10 ppm oxygen as alcohol.

9. The process according to claim 8, wherein the component containing the at least one primary or secondary alkyl alcohol is added such that the distillate fuel blend composition contains between about 100 ppm and about 1 wt. % oxygen as alcohol.

10. The process according to claim 9, wherein the component containing the at least one primary or secondary alkyl alcohol is added such that the distillate fuel blend composition contains between about 1000 ppm and about 0.5 wt. % oxygen as alcohol.

* * * * *